(12) United States Patent
Pillot et al.

(10) Patent No.: US 10,088,465 B2
(45) Date of Patent: Oct. 2, 2018

(54) METHOD FOR DETERMINING QUANTITIES OF HYDROCARBON COMPOUNDS CONTAINED IN ROCK FROM A GEOLOGICAL SAMPLE

(71) Applicant: IFP Energies nouvelles, Rueil-Malmaison (FR)

(72) Inventors: Daniel Pillot, St Germain en Laye (FR); Geremie Letort, Vienne (FR); Maria-Fernanda Romero-Sarmiento, Rueil-Malmaison (FR); Violaine Lamoureux-Var, Chatou (FR); Valerie Beaumont, Montreuil sous Bois (FR); Bruno Garcia, Neuilly sur Seine (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 15/845,710

(22) Filed: Dec. 18, 2017

(65) Prior Publication Data

US 2018/0106776 A1 Apr. 19, 2018

Related U.S. Application Data

(63) Continuation of application No. 14/725,483, filed on May 29, 2015.

(30) Foreign Application Priority Data

Nov. 3, 2014 (FR) .................................... 14/60.576

(51) Int. Cl.
*G01N 25/00* (2006.01)
*G01N 33/24* (2006.01)
(Continued)

(52) U.S. Cl.
CPC ........... *G01N 33/241* (2013.01); *G01N 25/00* (2013.01); *G01V 9/005* (2013.01); *G01N 33/004* (2013.01);
(Continued)

(58) Field of Classification Search
CPC .. G01N 33/241; G01N 25/00; G01N 21/3563; G01N 2203/0694; G01N 33/004;
(Continued)

(56) References Cited

U.S. PATENT DOCUMENTS 3,895,080 A * 7/1975 Davis ..................... C07C 7/13
208/310 R
5,786,225 A 7/1998 Lafargue et al.
(Continued)

FOREIGN PATENT DOCUMENTS

| EP | 0691540 A1 | 1/1996 |
| EP | 0829719 A1 | 3/1998 |
| FR | 2472754 A1 | 7/1981 |

OTHER PUBLICATIONS

French Search Report with Written Opinion for FR Application No. 1455009 dated Apr. 20, 2014.
(Continued)

*Primary Examiner* — Sujoy Kundu
*Assistant Examiner* — Lynda Dinh
(74) *Attorney, Agent, or Firm* — Fitch, Even, Tabin & Flannery LLP (57) ABSTRACT

The invention is a method of assessing at least one petroleum characteristic of a rock sample. Starting from a temperature ranging between 50° C. and 120° C., the temperature of a rock sample is raised to a temperature ranging between 180° C. and 220° C. which is maintained for a predetermined time duration. The temperature of the sample is increased to a temperature ranging between 330° C. and
(Continued)

370° C. which is maintained for a predetermined time duration. The temperature of the sample is then raised to a temperature ranging between 630° C. and 670° C. Three quantities representative of the amount of hydrocarbon compounds released during the temperature change stages are measured and at least one petroleum characteristic of the sample is deduced from these quantities.

30 Claims, 2 Drawing Sheets

(51) Int. Cl.
  *G01V 9/00* (2006.01)
  *G01N 33/00* (2006.01)
(52) U.S. Cl.
  CPC . *G01N 33/0047* (2013.01); *G01N 2203/0694* (2013.01)
(58) Field of Classification Search
  CPC ... G01N 33/0047; G01N 25/005; G01V 9/005
  USPC .......................................................... 702/2
  See application file for complete search history.

(56) References Cited

U.S. PATENT DOCUMENTS

| | | | |
|---|---|---|---|
| 5,843,787 A | 12/1998 | Trabelsi et al. | |
| 6,048,497 A | 4/2000 | Lafargue et al. | |
| 6,823,298 B1 * | 11/2004 | Jones | G01N 33/2823 703/10 |
| 2004/0152587 A1 * | 8/2004 | Creyghton | B01J 29/084 502/64 |

OTHER PUBLICATIONS

Frank D. Mango et al., "Low-Temperature Gas from Marine Shales", Geochemical Transations, Bio Med Central Ltd., London, GB vol. 10, Feb. 23, 2009, pp. 1-8, XP021047220.
E. Lafargue et al., "Rock-Eval 6 Applications in Hydrocarbon Exploration, Production and in Soil Contamination Studies", In Revue de l'Institut Francais de Pétrole vol. 53, No. 4, pp. 421-437.
F. Behar et al., "Rock-Eval 6 Technology: Performances and Developments", Oil & Gas Science and Technology, Rev. IFP, vol. 56 (2001), No. 2, pp. 111-134.

* cited by examiner

METHOD FOR DETERMINING QUANTITIES OF HYDROCARBON COMPOUNDS CONTAINED IN ROCK FROM A GEOLOGICAL SAMPLE

CROSS REFERENCE TO RELATED APPLICATIONS

This application is a continuation of U.S. patent application Ser. No. 14/725,483 which application is incorporated herein by reference in its entirety; and Reference is made to French Patent Application Serial No. 14/60.576, filed Nov. 3, 2014, and French Patent Application Serial No. 14/55.009, filed Jun. 3, 2014, which applications are incorporated herein by reference in their entirety.

BACKGROUND OF THE INVENTION

Field of the Invention

The present invention relates to the petroleum industry and more particularly exploration and exploitation of a potentially or truly hydrocarbon-producing geological formation.

Description of the Prior Art

Petroleum compounds, mainly hydrocarbons extractable using organic solvents, form through the transformation of insoluble organic matter (known as kerogen) generated by the temperature and pressure rise inherent in the burial of sediments in a sedimentary basin. Sedimentary rocks that have generated petroleum are referred to as source rocks. Under certain conditions, the petroleum thus formed is partly expelled from the source rock and migrates to rocks known as reservoir rocks where it accumulates.

Source rocks have long been considered as an unexploitable source of hydrocarbons. This is no longer the case with the evolution of technology. Indeed, hydrocarbons from source rocks represent a new source of fossil energy today. For this type of hydrocarbon, the source rock is also the reservoir rock, the hydrocarbons remaining trapped and disseminated within a very low-permeability rock. Source rock hydrocarbons are categorized in the family of unconventional hydrocarbons, their extraction requiring unconventional techniques in relation to those commonly used in the oil and gas industry. This type of source rock is known as hydrocarbon source rock (shale plays).

Knowing the soluble organic matter (petroleum), on the one hand, and the insoluble organic matter (kerogen), on the other hand, present in a rock sample is of great interest in oil exploration and exploitation. Indeed, it is for example well known that:

The amount of petroleum formed in the sediments regularly increases with the depth of burial. It is therefore possible to assess the degree of evolution of the organic matter contained in these sediments and, more particularly, the interval of evolution that corresponds to the main stage of petroleum formation, The nature of the insoluble organic matter contained in the rocks conditions the petroleum-generating potential of these rocks, that is, their more or less high capacity to produce petroleum.

Thus, knowledge of such data allows drilling to carry out long, costly and perilous coring or reservoir testing operations only advisedly, especially when these results can be acquired simultaneously with the drilling operations.

The following documents are mentioned in the description below:

Behar, F., Beaumont, V., De B. Penteado, H. L., 2001. Rock-Eval 6 Technology: Performances and Developments. Oil & Gas Science and Technology 56, 111-134;

Lafargue, E., Marquis, F., Pillot, D., 1998. Rock-Eval 6 Applications in Hydrocarbon Exploration, Production, and Soil Contamination Studies. Oil & Gas Science and Technology—Revue de l'Institut Français du Pétrole, 53, 4, 421-437.

The known ROCK-EVAL® technique (IFP Energies nouvelles, France) developed by the applicant is notably described in French Patent No. 2,472,754 and European Patent No. 0,691,540. This analysis technique, which is fast and almost automatic, has been developed for characterizing the organic matter and the hydrocarbons contained in a rock sample from a geological formation. More precisely, this technique allows determination of the presence, the nature and the degree of maturity of the organic matter contained in a rock sample. The ROCK-EVAL method also provides precise information on the quantification of hydrocarbons, the amount of total organic carbon (TOC) and the amount of mineral carbon (MinC) contained in a rock sample.

The ROCK-EVAL technique involves the pyrolysis in an inert (non-oxidizing) atmosphere, according to a predetermined temperature sequence, of a rock sample. The pyrolysis oven cooperates with a device for detecting and measuring the amount of hydrocarbon compounds in the pyrolyzed sample. The specific detection device comprises for example a flame ionization type detector conventionally used in gas chromatography analyses. The detector delivers a signal representative of the amounts of hydrocarbon products measured. This signal can be transmitted to computation, storage and display means wherein a specific software computes, displays and stores the various parameters representative of the characteristics of the hydrocarbons present. More details concerning the ROCK-EVAL technique are given in the aforementioned documents.

Thus, the ROCK-EVAL technique allows in particular measuring the amount of hydrocarbon compounds released throughout the pyrolysis. A pyrogram can then be established, which is a curve showing the evolution of the amount of released hydrocarbon compounds in relation to the weight of the sample being considered, as a function of time. A pyrogram generally has several peaks (see for example FIGS. 1A and 1B). The peaks are well differentiated and the surface area of each peak is calculated. A quantity representative of the amount of hydrocarbon compounds released within the temperature range bounding the peak considered is thus obtained for each peak.

Two main methods using two different temperature sequences have been developed:

The Basic or Bulk Rock method, more particularly dedicated to source rock samples, is for example described in Lafargue et al. (1998) and Behar et al. (2001). The temperature sequence of this method is characterized by an initial temperature $T_1$ of the pyrolysis oven generally ranging between 300° C. and 350° C., a temperature that is maintained for a predetermined time duration of the order of some minutes. It is during this stage that the free hydrocarbons initially contained in the rock sample are released. Their amount is estimated by measuring the surface area of a first peak, denoted by $S_1$. The pyrolysis temperature is then progressively raised to a temperature $T_2$ of generally 550° C. This stage involves the volatilization of the very heavy hydrocarbon compounds and the cracking of the non-volatile organic matter. The amount of hydrocarbon compounds released during this thermal cracking stage is assessed by measuring the surface area of a second peak, denoted by $S_2$. It corresponds to the amount of hydrocarbon compounds that would have been generated if the rock had reached a sufficient maturation stage;

The Reservoir method, more particularly dedicated to reservoir rock samples, is for example described in European Patent No. 0,691,540. The temperature sequence of the Reservoir method is characterized by an initial temperature T1 of the pyrolysis oven below 200° C. and preferably equal to 180° C. This temperature is maintained for a predetermined time duration and the amount of light hydrocarbon compounds is assessed by measuring the surface area of a first peak, denoted by $S_{1r}$. The temperature of the pyrolysis oven is then raised to a second temperature T2 of about 370° C., a stage wherein the amount of heavier hydrocarbons released is estimated by assessing the surface area of a second peak, denoted by $S_{2a}$. Temperature T2 substantially corresponds to the end of the thermovaporization of some hydrocarbons and to the start of cracking through pyrolysis of the heavy compounds. Thus, the family of hydrocarbon compounds corresponding to peaks $S_{1r}$ and $S_{2a}$ of the Reservoir method is nearly equivalent to the family of hydrocarbon compounds characteristic of peak $S_1$ of the Basic method. The pyrolysis temperature is then increased again to a third temperature T3 of at most 800° C. The surface area of a third peak, denoted by $S_{2b}$, representative of the heavy hydrocarbon compounds, is estimated during this third heating stage. This peak $S_{2b}$ can be considered as an equivalent of peak $S_2$ of the Basic method.

Figure 1A:
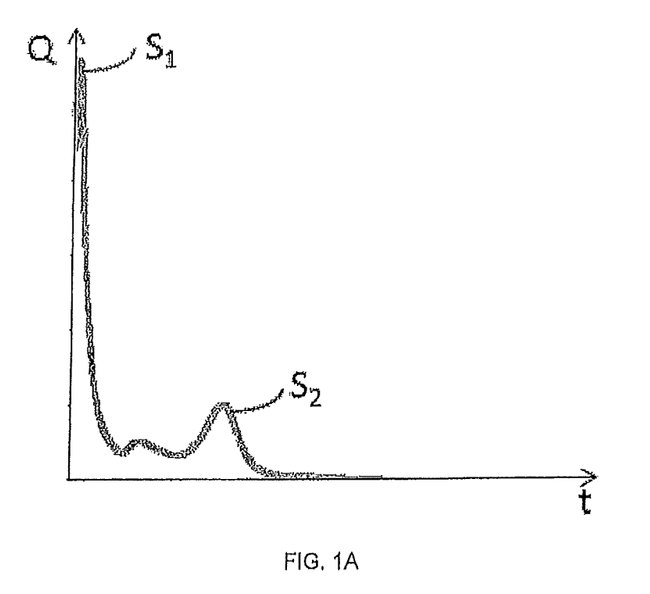
FIGS. 1A and 1B show the evolution of the amount of hydrocarbon compounds (Q) over time (t) during a pyrolysis, established according to the Basic method and to the Reservoir method respectively for the same hydrocarbon source rock sample. It can be noted that the X-axis representing time is given on an indicative basis: the position of the peaks in relation to the X-axis cannot be directly compared because the temperature sequences are different from one method to the other.
Figure 1B:
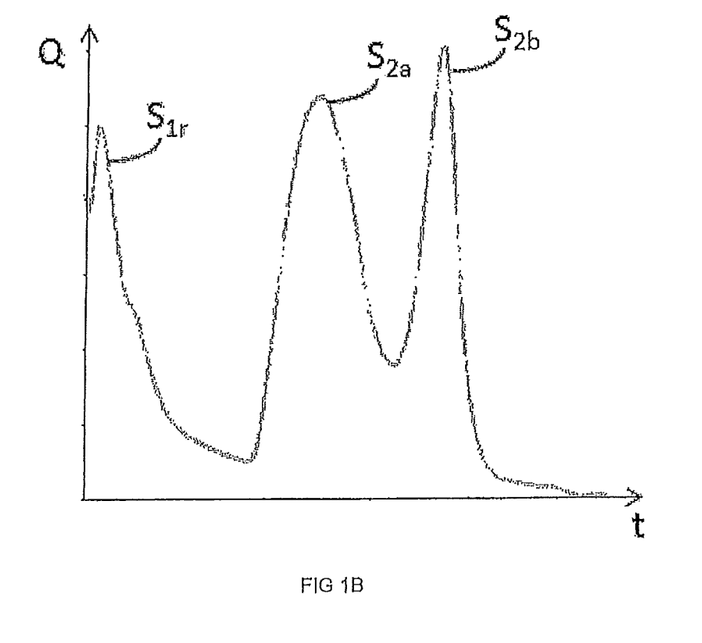

Although initially developed for particular rock types (source rock for the Basic method and reservoir rock for the Reservoir method), these two methods can however be applied to any rock type. Applied to samples of hydrocarbon source rock type, it appears that both methods underestimate the surface area of the peak(s) corresponding to the free hydrocarbons contained in the sample considered. Indeed, as illustrated in FIGS. 1A and 1B showing the pyrograms resulting from the application of the Basic method and of the Reservoir method respectively to the same hydrocarbon source rock sample, the first peak is truncated. The quantification of the surface area thereof is therefore underestimated, as well as the amount of free hydrocarbon compounds contained in this rock.

Thus, it appears that the temperature sequences of the Basic and Reservoir methods are in particular not suitable for hydrocarbon source rock samples. This can be explained by the fact that, when these methods have been developed, source rocks were not considered to be exploitable petroleum reservoirs.

Due to the growing interest in source rock hydrocarbons, there is a high demand for an improvement in the ROCK-EVAL pyrolysis technique allowing to reliably assess the amount of free hydrocarbons in a hydrocarbon source rock, and more generally the amount of hydrocarbons potentially extractable from this type of rock.

SUMMARY OF THE INVENTION

The present invention relates to a pyrolysis method allowing improvement of the quantification of hydrocarbon compounds contained in a rock sample. In particular, the temperature sequence applied in the present invention is suited for hydrocarbon source rocks. Furthermore, some petroleum characteristics allow evaluation of the interest of exploring and/or developing a given geological formation are predefined.

The invention relates to a method of assessing at least one petroleum characteristic of a rock sample from a geological formation, wherein the sample is heated in an inert atmosphere according to a temperature sequence. The method comprises the following stages:

a) from a first temperature value (T1) ranging between 50° C. and 120° C., raising the temperature of the sample, according to a first temperature gradient ranging between 1° C./min and 50° C./min, to a second temperature value (T2) ranging between 180° C. and 220° C., and maintaining the sample at the second temperature value (T2) for a first predetermined time duration;

b) from the second temperature value (T2), raising the temperature of the sample according to a second temperature gradient ranging between 1° C./min and 50° C./min to a third temperature value (T3) ranging between 330° C. and 370° C., and maintaining the sample at the third temperature value (T3) for a second predetermined time duration;

c) from the third temperature value (T3), raising the temperature of the sample according to a third temperature gradient ranging between 1° C./min and 50° C./min to a fourth temperature value (T4) ranging between 630° C. and 670° C.;

d) determining quantities $S_{h0}$, $S_{h1}$ and $S_{h2}$ representative of the measured amount of hydrocarbon compounds released in stages a, b and c respectively;

e) determining, from at least one of the quantities $S_{h0}$, $S_{h1}$ and $S_{h2}$, at least one petroleum characteristic of the sample.

In one embodiment of the present invention, the rock sample can come from a hydrocarbon source rock.

According to an advantageous embodiment, the first temperature can range between 80° C. and 120° C.

According to another advantageous embodiment, the first temperature can range between 90° C. and 110° C.

Advantageously, at the start of stage a), the sample can be maintained at the first temperature T1.

According to a preferred embodiment, the second temperature can range between 190° C. and 210° C.

According to another preferred embodiment, the third temperature can range between 340° C. and 360° C.

Advantageously, the fourth temperature can range between 640° C. and 660° C.

Preferably, the first and second time durations can range between 2 and 4 minutes.

Advantageously, the first, second and third temperature gradients can range between 20° C./min and 30° C./min.

According to an embodiment of the present invention, the petroleum characteristic of the sample calculated in stage e) can be selected from among: a free hydrocarbon content index denoted by $HC_{cont}$, a quality index of the hydrocarbons denoted by HQI, a production index denoted by $PI_{Shale}$, the API degree, the GOR parameter and the GCR parameter.

According to an embodiment of the present invention, a free hydrocarbon content index $HC_{cont}$ can be calculated in stage e) according to the formula as follows:

$$HC_{cont} = S_{h0} + S_{h1}$$

with $S_{h0}$, $S_{h1}$ and $HC_{cont}$ expressed in milligram of hydrocarbon compound per gram of rock.

According to another embodiment of the present invention, a quality index HQI of the hydrocarbons can be calculated in stage e) according to the formula as follows:

$$HQI = \frac{S_{h0}}{S_{h0} + S_{h1}} \times 100$$

with $S_{h0}$ and $S_{h1}$ expressed in milligram of hydrocarbon compound per gram of rock and HQI expressed as percentage by mass.

According to a particular embodiment of the present invention, a production index $PI_{Shale}$ can be calculated in stage e) according to the formula as follows:

$$PI_{Shale} = \frac{(S_{h0} + S_{h1})}{(S_{h0} + S_{h1} + S_{h2})} \times 100$$

with $S_{h0}$, $S_{h1}$ and $S_{h2}$ expressed in milligram of hydrocarbon compound per gram of rock, and $PI_{Shale}$ expressed as percentage by mass.

Advantageously, the calculation of the production index $PI_{Shale}$ can be repeated for the samples from different sedimentary layers of the formation, and at least one sedimentary layer of the formation of interest with a view to oil exploration and/or exploitation can be determined when the production index $PI_{Shale}$ is greater by a factor λ than the average of all of the production indices $PI_{Shale}$ measured for the formation.

Preferably, said factor λ can range between 1.1 and 1.5.

BRIEF DESCRIPTION OF THE DRAWINGS

Other features and advantages of the method according to the invention will be clear from reading the description hereafter of embodiments given by way of non-limitative example, with reference to the accompanying figures wherein.

DETAILED DESCRIPTION OF THE INVENTION

The present invention is a method of assessing at least one petroleum characteristic of a rock sample from a geological formation, wherein sample is heated in an inert atmosphere according to a particular temperature sequence. The present invention is applicable to any rock type such as, for example, a source rock, a reservoir rock or a hydrocarbon source rock. The advantages of the method according to the invention are shown hereafter within the context of an application to a rock sample from a hydrocarbon source rock.

Thus, the present invention comprises at least the following stages:

a) from a first temperature value (T1) ranging between 50° C. and 120° C., raising the temperature of the sample, according to a first temperature gradient ranging between 1° C./min and 50° C./min, to a second temperature value (T2) ranging between 180° C. and 220° C., and maintaining the sample at the second temperature value (T2) for a first predetermined time duration;

b) from the second temperature value (T2), raising the temperature of the sample according to a second temperature gradient ranging between 1° C./min and 50° C./min to a third temperature value (T3) ranging between 330° C. and 370° C., and maintaining the sample at the third temperature value (T3) for a second predetermined time duration;

c) from the third temperature value (T3), raising the temperature of the sample according to a third temperature gradient ranging between 1° C./min and 50° C./min to a fourth temperature value (T4) ranging between 630° C. and 670° C.;

d) determining quantities $S_{h0}$, $S_{h1}$ and $S_{h2}$ representative of the measured amount of hydrocarbon compounds released in stages a, b and c respectively;

e) determining, from at least one of the three quantities $S_{h0}$, $S_{h1}$ and $S_{h2}$, at least one petroleum characteristic of the sample.

Figure 2:
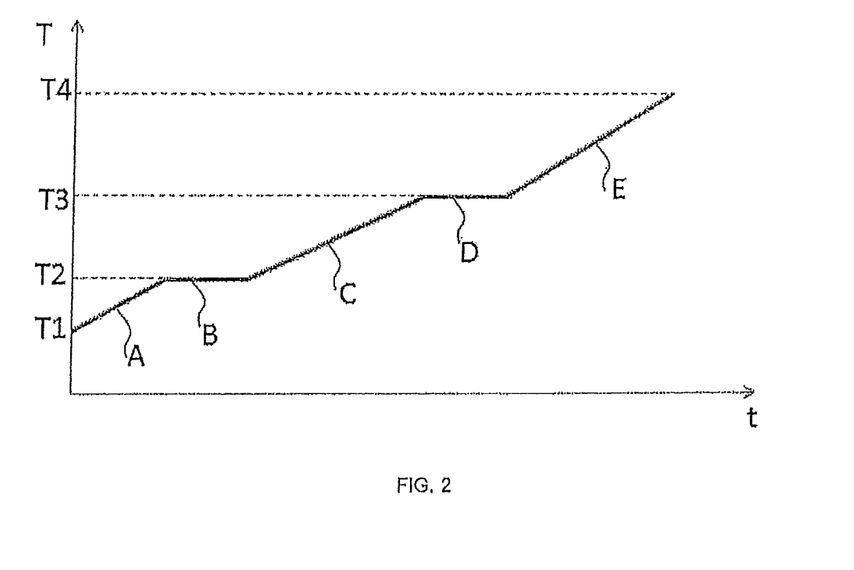
FIG. 2 illustrates the temperature sequence of the method according to the invention.

FIG. 2 illustrates the temperature sequence of the pyrolysis operation in an inert atmosphere according to the method of the invention.

At the beginning of the process, the sample is fed into the oven heated at a first temperature (T1). This initial temperature value (T1) ranges between 50° C. and 120° C. According to a preferred embodiment of the invention, first temperature (T1) ranges between 80° C. and 120° C. According to another embodiment of the present invention, first temperature (T1) ranges between 90° C. and 110° C.

According to an embodiment of the present invention, the sample is maintained at first temperature (T1) for a non-zero-time duration. This preliminary stage of maintaining the sample at first temperature (T1) allows warming up of the sample and/or release of the very light hydrocarbon compounds present in a slightly damaged or undamaged sample.

The sample is then subjected to a programmed heating phase where the temperature rise ranges between 1° C./min and 50° C./min (segment A), up to a temperature corresponding to a second temperature (T2) ranging between 180° C. and 220° C. Advantageously, a second temperature (T2) ranging between 190° C. and 210° C. is selected. The temperature gradient preferably ranges between 20° C./min and 30° C./min.

The sample is maintained at second temperature (T2) for a first predetermined non-zero-time duration (segment B) greater than a half-minute for example and preferably ranging between 2 and 4 minutes. This second temperature (T2) substantially corresponds to the end of the thermovaporization stage of the lighter hydrocarbons contained in the rock sample and to the start of the stage of cracking through pyrolysis of the heavier hydrocarbons.

Then, from second temperature (T2), the temperature is raised (segment C) up to a temperature corresponding to a third temperature (T3) according to a temperature gradient ranging between 1° C./min and 50° C./min. The value of third temperature (T3) ranges between 330° C. and 370° C. Advantageously, a third temperature value between 340° C.

and 360° C. is selected. According to a preferred embodiment, the temperature gradient ranges between 20° C./min and 30° C./min.

Third temperature (T3) is maintained (segment D) for a predetermined non-zero-time duration greater than a half-minute for example and preferably ranging between 2 and 4 minutes. This third temperature (T3) substantially corresponds to the end of the thermovaporization stage of the heavy hydrocarbons contained in the rock sample and to the start of the stage of cracking through pyrolysis of the very heavy hydrocarbons.

Pyrolysis is continued (segment E) so as to reach a fourth temperature (T4) according to a temperature gradient ranging between 1° C./min and 50° C./min. The value of fourth temperature (T4) ranges between 630° C. and 670° C., preferably between 640° C. and 660° C. The temperature gradient advantageously ranges between 20° C./min and 30° C./min. This fourth temperature (T4) substantially corresponds to the end of the pyrolysis stage, that is, the end of the thermal cracking of the organic matter present in the rock sample.

Thus, the temperature sequence of the method according to the invention comprises a succession of three heating stages (ramps illustrated by segments A, C and E in FIG. 2) separated by two temperature maintenance stages (isothermal stages illustrated by segments B and D in FIG. 2).

Figure 3:
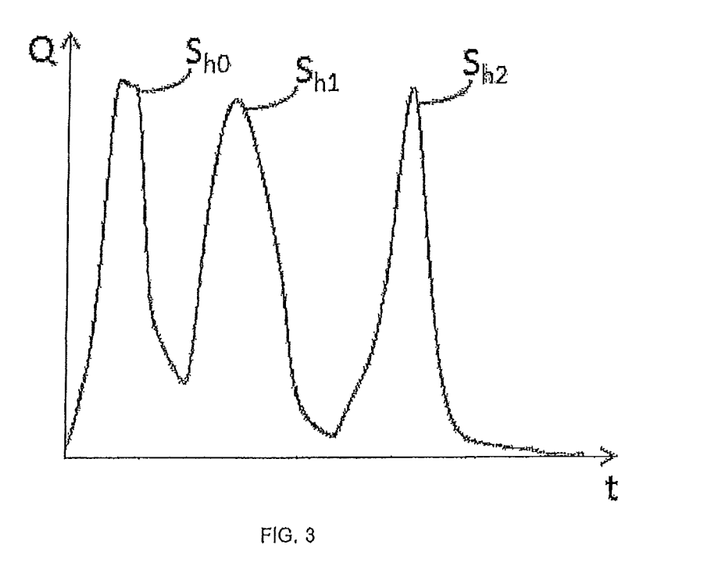
FIG. 3 illustrates the evolution of the amount of hydrocarbon compounds (Q) over time (t) during a pyrolysis, established according to the method of the invention on a hydrocarbon source rock sample, the sample being identical to the one used in FIGS. 1A and 1B. It can be noted that the X-axis representing time is given on an indicative basis: the position of the peaks in relation to the X-axis cannot be directly compared because the temperature sequences are different from one method to the other.

FIG. 3 shows the pyrogram resulting from the application of the method according to the invention to the same hydrocarbon source rock sample as the one considered for establishing FIGS. 1A and 1B. It can be observed in FIG. 3 that the pyrogram is characterized by the presence of three peaks: a first peak referred to as peak $S_{h0}$, a second peak referred to as peak $S_{h1}$ and a third peak referred to as peak $S_2$.

The surface area of peak $S_{h0}$, given for example in milligram of hydrocarbon compounds per gram of rock, corresponds to the amount of hydrocarbon compounds obtained between first temperature (T1) and second temperature (T2), more precisely obtained during segments A and B of FIG. 2. This quantity, referred to as quantity $S_{h0}$, is representative of the lightest thermovaporizable hydrocarbons.

The surface area of peak $S_{h1}$, given for example in milligram of hydrocarbon compounds per gram of rock, corresponds to the amount of hydrocarbon compounds obtained between second temperature (T2) and third temperature (T3), more precisely obtained during segments C and D of FIG. 2. This quantity, referred to as quantity $S_{h1}$, is representative of the heavy thermovaporizable hydrocarbons.

The surface area of peak $S_{h2}$, given for example in milligram of hydrocarbon compounds per gram of rock, corresponds to the amount of hydrocarbon compounds obtained between third temperature (T3) and fourth temperature (T4), more precisely obtained during segment E of FIG. 2. This quantity, referred to as quantity $S_{h2}$, is representative of the very heavy thermovaporizable hydrocarbons.

It can be observed in FIG. 3 that the method according to the invention allows obtaining a first complete, non-truncated peak (peak $S_{h0}$), unlike the Basic (peak $S_1$ in FIG. 1A) and Reservoir (peak $S_{1r}$ in FIG. 1B) methods. The method according to the invention thus allows more exhaustive recording of the free hydrocarbons contained in a sample and therefore, more generally, better quantification of the hydrocarbon compounds contained in a sample. Furthermore, the method according to the invention allows better separation of the last peak (peak $S_{h2}$) than in the case of the Reservoir method (peak $S_{2b}$ in FIG. 1B) or in the case of the Basic method (peak $S_2$ in FIG. 1A).

Thus, the advantages of the method according to the invention shown in the above example are explained by the temperature sequence characteristic of the method according to the invention. Indeed, as the temperature sequence starts at a first low temperature (T1) in relation to the prior art methods, the method according to the invention allows measuring more completely the amount of free hydrocarbon compounds present in a sample. Furthermore, the method of the invention comprising, between two heating stages (ramps A, C and E in FIG. 2), temperature maintenance stages (isothermal stages B and D in FIG. 2) of duration at least greater than one half-minute, these isothermal stages allow ensuring the end of the thermovaporization of the hydrocarbon compounds of interest in the temperature range considered.

From at least one of these three quantities, at least one petroleum characteristic of the source rock sample considered is calculated.

According to an embodiment of the present invention, a free hydrocarbon content index $HC_{cont}$ is calculated according to the formula as follows:

$$HC_{cont} = S_{h0} + S_{h1}$$

with $S_{h0}$, $S_{h1}$ and $HC_{cont}$ expressed in milligram of hydrocarbons per gram of rock.

According to another embodiment of the present invention, a quality index HQI of the hydrocarbons is calculated according to the formula as follows:

$$HQI = \frac{S_{h0}}{S_{h0} + S_{h1}} \times 100$$

with $S_{h0}$ and $S_{h1}$ expressed in milligram per gram of rock. HQI represents the proportion, expressed as percentage by mass, of very light hydrocarbons in relation to the thermovaporizable fraction.

Advantageously, a production index $PI_{Shale}$ is calculated according to the formula as follows:

$$PI_{Shale} = \frac{(S_{h0} + S_{h1})}{(S_{h0} + S_{h1} + S_{h2})} \times 100$$

with $S_{h0}$, $S_{h1}$ and $S_{h2}$ expressed in milligram per gram of rock. Index $PI_{Shale}$, expressed as percentage by mass, represents the quantity relative to the light hydrocarbon fraction in relation to all of the pyrolyzable hydrocarbons (thermovaporizable hydrocarbons plus those starting to be thermocracked).

According to an embodiment of the present invention wherein the assessment of index $PI_{Shale}$ is repeated for rock samples from different sedimentary layers of a geological formation, the sedimentary layer(s) of the geological formation of interest with a view to oil exploration and/or exploitation are determined when their production index $PI_{Shale}$ is greater by a factor λ than the average of all the production indices $PI_{Shale}$ measured for the geological formation considered. According to a preferred embodiment of the invention, a value ranging between 1.1 and 1.5 is selected for factor λ.

According to an embodiment of the present invention, it is also possible to calculate, from said three quantities, a petroleum characteristic of the source rock sample considered, such as:

The API degree: it is a scale known to the person skilled in the art, which is a measure of the gravity of a crude oil; thus, the lighter a crude oil, the lower the gravity and the higher the API degree thereof. Most crudes have API degrees ranging between 20° (very heavy) and 60° (very light);

The GOR (Gas/Oil Ratio) parameter: this measure is known to the person skilled in the art expresses the amount of gas produced at the wellhead in relation to the amount of oil;

The GCR (Gas/Condensate Ratio) parameter: this measure is known to the person skilled in the art expresses the amount of condensates (or light hydrocarbons) in relation to the amount of gas.

APPLICATION EXAMPLES

Table 1 compares the results obtained with the method according to the invention (referred to as Method 1) and the Reservoir method (referred to as Method 2) on three rock samples (referred to as sample A, B and C) from different hydrocarbon source rock types. In the case of the Reservoir method, equivalences denoted by $HC^*_{cont}$, $HQI^*$ and $PI^*_{shale}$ for petroleum characteristics $HC_{cont}$, $HQI$ and $PI_{shale}$ defined above for the method according to the invention were calculated as follows:

- $HC^*_{cont} = S_{1r} + S_{2a}$;

- $HQI^* = \dfrac{S_{1r}}{S_{1r} + S_{2a}} \times 100$;

- $PI^*_{shale} = \dfrac{(S_{1r} + S_{2a})}{(S_{1r} + S_{2a} + S_{2b})} \times 100$.

According to this table, it can be observed that, whatever the sample under consideration, the value of the petroleum characteristic $HC_{cont}$ obtained with the method according to the invention is greater than its equivalent $HC^*_{cont}$ obtained with the Reservoir method. Indeed, as shown in Table 1, characteristic $HC_{cont}$ is 30% greater than its equivalent $HC^*_{cont}$ in the case of sample A, 40% in the case of sample B and 28% in the case of sample C. Thus, this means that the method according to the invention allows measuring a larger amount of free hydrocarbons contained in the sample considered. As a result, by means of a temperature sequence starting with a lower temperature than the Reservoir method, the method according to the invention allows better assessment of the amount of the free hydrocarbons present in a rock sample from a hydrocarbon source rock than the prior art.

As regards petroleum characteristics $HQI$ and $PI_{shale}$, no systematic trend can be observed from one sample to the next. This is explained by the fact that these characteristics depend on the proportion of the hydrocarbon types (free, thermovaporizable, thermocrackable) present in the sample considered respectively.

Table 2 compares the measured quantities $S_{h0}$, $S_{h1}$ and $S_{h2}$ (corresponding to the surface areas of peaks $S_{h0}$, $S_{h1}$ and $S_{h2}$ respectively), as well as some petroleum characteristics ($HC_{cont}$, $HQI$ and $PI_{shale}$) obtained with the method of the invention applied to a rock sample containing source rock hydrocarbons, implemented with the following values for the first, second, third and fourth temperatures:

case 1: T1=100° C., T2=200° C., T3=350° C. and T4=650° C.;

case 2: T1=80° C., T2=200° C., T3=350° C. and T4=650° C.;

case 3: T1=100° C., T2=180° C., T3=350° C. and T4=650° C.;

case 4: T1=100° C., T2=220° C., T3=350° C. and T4=650° C.

It can be seen in Table 2 that petroleum characteristic $HC_{cont}$ is equivalent (to within 1.7%, which is the order of magnitude of the measurement uncertainty) in cases 1 or 2. This shows that the free hydrocarbons contained in a rock sample are recovered in an equivalent manner when applying the method according to the invention either with the central temperature or with the minimum temperature of the preferred first temperature range relative to first temperature T1.

It can also be observed in Table 2 that measured quantity $S_{h0}$ varies greatly in cases 3 and 4. Thus, the value of second temperature T2, corresponding to the end of the first heating ramp and to the first temperature stage of the temperature sequence implemented in the present invention, has a significant impact on quantity $S_{h0}$. Indeed, at 180° C., all the light free hydrocarbons have not been thermovaporized yet ($S_{h0}$ is 1.59 mg/g rock) whereas at 220° C., thermovaporization of part of the heavier free hydrocarbons has started ($S_{h0}$ is 2.5 mg/g rock). On the other hand, once again, the value of petroleum characteristic $HC_{cont}$ is equivalent in cases 3 and 4 (to within 0.01 mg/g rock, which is below the measurement uncertainty). This shows that the free hydrocarbons contained in a rock sample are recovered in an equivalent manner when applying the method according to the invention either with the minimum temperature or with the maximum temperature of the temperature range relative to second temperature T2.

TABLE 1

| Method 1 | $S_{h0}$ (mg/g) | $S_{h1}$ (mg/g) | $S_{h2}$ (mg/g) | $HC_{cont}$ (mg/g) | $HQI$ (mass %) | $PI_{Shale}$ (mass %) |
|---|---|---|---|---|---|---|
| Sample A | 1.72 | 3.03 | 2.39 | 4.75 | 36.21 | 66.53 |
| Sample B | 5.03 | 7.50 | 96.04 | 12.53 | 40.14 | 11.54 |
| Sample C | 0.91 | 2.75 | 6.33 | 3.66 | 24.86 | 36.64 |

| Method 2 | $S_{1r}$ (mg/g) | $S_{2a}$ (mg/g) | $S_{2b}$ (mg/g) | $HC^*_{cont}$ (mg/g) | $HQI^*$ (mass %) | $HQI^*$ (mass %) |
|---|---|---|---|---|---|---|
| Sample A | 1.25 | 2.04 | 1.25 | 3.29 | 37.99 | 72.47 |
| Sample B | 3.33 | 4.29 | 95.70 | 7.62 | 43.70 | 7.38 |
| Sample C | 0.70 | 1.93 | 6.97 | 2.63 | 26.62 | 27.40 |

TABLE 2

| | Sh0 (mg/g) | Sh1 (mg/g) | Sh2 (mg/g) | HCcont (mg/g) | HQI (mass %) | PIShale (mass %) |
|---|---|---|---|---|---|---|
| Case 1 | 1.94 | 2.85 | 2.51 | 4.79 | 40.50 | 65.62 |
| Case 2 | 1.89 | 2.82 | 2.44 | 4.71 | 40.13 | 65.87 |
| Case 3 | 1.59 | 3.31 | 2.54 | 4.90 | 32.45 | 65.86 |
| Case 4 | 2.50 | 2.41 | 2.53 | 4.91 | 50.92 | 65.99 |

OTHER EMBODIMENTS

According to a particular embodiment of the present invention, a rock sample from a geological formation is heated in a non-oxidizing atmosphere with the temperature sequence as defined in the method according to the invention, and the amount of hydrocarbon compounds released during the heating stage is continuously measured using a first detector, as well as the amount of $CO_2$ and of CO contained in the effluent resulting from the heating stage, using a second detector. According to one embodiment of the present invention, from the continuous $CO_2$ measurements, the amount of $CO_2$ of organic origin and the amount of $CO_2$ of mineral origin is determined. According to another embodiment of the present invention, from the continuous $CO_2$ and CO measurements, the amount of oxygen of organic origin and the amount of oxygen of mineral origin is determined. According to another embodiment of the present invention, the residues resulting from heating in a non-oxidizing atmosphere are placed in another oven where they are heated in an oxidizing atmosphere. According to an embodiment of the present invention, heating in an oxidizing atmosphere can be temperature programmed so as to raise the temperature from approximately 400° C. to approximately 850° C. with a temperature gradient ranging between 10 and 30° C./min. According to an embodiment of the present invention, the amount of $CO_2$ and/or of CO contained in the effluent resulting from heating in an oxidizing atmosphere is continuously measured. According to an embodiment of the present invention, from the continuous $CO_2$ measurements in an oxidizing atmosphere, the amount of $CO_2$ of organic origin and the amount of $CO_2$ of mineral origin is determined. According to another embodiment of the present invention, the amount of total organic carbon contained in the sample is determined from the $CO_2$ and CO measurements obtained after heating sequences in non-oxidizing and oxidizing atmospheres. According to an embodiment of the present invention, the device used for implementing the present invention comprises a single oven allowing heating in an oxidizing atmosphere and heating in a non-oxidizing atmosphere.

The invention claimed is:

1. A method for determining quantities of hydrocarbon compounds contained in rock obtained from a geological sample by pyrolysis of the rock from the geological sample, by heating the sample in an inert atmosphere during a temperature sequence, comprising:
   a) raising a temperature of the rock from the geological sample from a first temperature ranging between 50° C. and 120° C., according to a first temperature gradient ranging between 1° C./min and 50° C./min, to a second temperature ranging between 180° C. and 220° C., maintaining the rock from the geological sample at the second temperature for a first predetermined time duration of greater than one half minute and measuring a quantity of hydrocarbons released from the rock from the geological sample during the heating of the rock from the geological sample for the first predetermined time duration;
   b) raising the temperature of the rock from the geological sample from the second temperature according to a second temperature gradient ranging between 1° C./min and 50° C./min to a third temperature ranging between 330° C. and 370° C., maintaining the rock from the geological sample at the third temperature for a second predetermined time duration of greater than one half minute and measuring a quantity of hydrocarbons released from the rock from the geological sample during the heating of the rock from the geological sample for the second predetermined duration;
   c) raising the temperature of the rock from the geological sample from the third temperature according to a third temperature gradient ranging between 1° C./min and 50° C./min to a fourth temperature ranging between 630° C. and 670° C. and measuring a quantity of hydrocarbons released from the rock from the geological sample during the heating of the rock from the geological sample from the third temperature until the fourth temperature is reached; and
   d) determining the quantities of hydrocarbon compounds contained in the rock from the geological sample from the measured quantities of hydrocarbon compounds released in step a), step b) and step c) respectively.

2. The method as claimed in claim 1, wherein the first temperature ranges between 80° C. and 120° C.

3. The method as claimed in claim 2, wherein the second temperature ranges between 190° C. and 210° C.

4. The method as claimed in claim 2, wherein the third temperature ranges between 340° C. and 360° C.

5. The method as claimed in claim 4, wherein the fourth temperature ranges between 640° C. and 660° C.

6. The method as claimed in claim 2, wherein the fourth temperature ranges between 640° C. and 660° C.

7. The method as claimed in claim 1, wherein the first temperature ranges between 90° C. and 110° C.

8. The method as claimed in claim 1, wherein at a start of step a), the rock from the geological sample is maintained at the first temperature.

9. The method as claimed in claim 1, wherein the second temperature ranges between 190° C. and 210° C.

10. The method as claimed in claim 1, wherein the third temperature ranges between 340° C. and 360° C.

11. The method as claimed in claim 1, wherein the fourth temperature ranges between 640° C. and 660° C.

12. The method as claimed in claim 1, wherein the first and second time durations range between 2 and 4 minutes.

13. The method as claimed in claim 1, wherein the first, second and third temperature gradients range between 20° C./min and 30° C./min.

14. A method of heating rock from a geological rock sample at successively higher temperature levels in an inert atmosphere and measuring amounts of hydrocarbon compounds in the geological rock sample which are successively released at each of the temperature levels and determining at least one petroleum characteristic from the measured amounts of hydrocarbon compounds comprising:
   a) raising a temperature of the rock from the geological rock sample from a first temperature ranging between 50° C. and 120° C., according to a first temperature gradient ranging between 1° C./min and 50° C./min, to a second temperature ranging between 180° C. and 220° C., and maintaining the rock from the geological rock sample at the second temperature for a first predetermined time duration of greater than one half minute and measuring a quantity of hydrocarbons released from the rock from the geological rock sample during the heating of the rock from the geological rock sample for the first predetermined time duration;
   b) raising the temperature of the rock from the geological rock sample from the second temperature according to a second temperature gradient ranging between 1° C./min and 50° C./min to a third temperature ranging between 330° C. and 370° C., and maintaining the rock from the geological rock sample at the third temperature for a second predetermined time duration of greater than one half minute and measuring a quantity of hydrocarbons released during the heating of the rock from the geological rock sample for the second predetermined duration;

c) raising the temperature of the rock from the geological rock sample from the third temperature according to a third temperature gradient ranging between 1° C./min and 50° C./min to a fourth temperature ranging between 630° C. and 670° C. and measuring a quantity of hydrocarbons released from the rock from the geological rock sample during the heating of the rock from the geological sample from the third temperature until the fourth temperature is reached;

d) determining quantities of hydrocarbon compounds contained in the rock from the geological rock sample from the measured quantities of hydrocarbons released in step a), step b) and step c) respectively and representative of the measured amounts of hydrocarbon compounds released in step a), step b) and step c) respectively; and e) assessing at least one petroleum characteristic of the geological rock sample from the determined quantities of hydrocarbon compounds contained in the geological rock sample.

15. The method as claimed in claim 14, wherein the first temperature ranges between 80° C. and 120° C.

16. The method as claimed in claim 15, wherein the first temperature ranges between 90° C. and 110° C.

17. The method as claimed in claim 14, wherein the first temperature ranges between 90° C. and 110° C.

18. The method as claimed in claim 17, wherein the second temperature ranges between 190° C. and 210° C.

19. The method as claimed in claim 14 wherein, at a start of step a), the rock from geological rock sample is maintained at the first temperature.

20. The method as claimed in claim 19, wherein the third temperature ranges between 340° C. and 360° C.

21. The method as claimed in claim 14, wherein the second temperature ranges between 190° C. and 210° C.

22. The method as claimed in claim 14, wherein the third temperature ranges between 340° C. and 360° C.

23. The method as claimed in claim 14, wherein the fourth temperature ranges between 640° C. and 660° C.

24. The method as claimed in claim 14, wherein the at least one petroleum characteristic of the rock from the geological rock sample assessed in step e) is selected from a free hydrocarbon content index denoted by a quality index of hydrocarbons, a production index, an API degree, a GOR parameter and a GCR parameter.

25. The method as claimed in claim 24, wherein the free hydrocarbon content index is calculated according to a formula as follows:

$$HC_{cont} = S_{h0} + S_{h1}$$

wherein $S_{h0}$, $S_{h1}$ and $S_{h0}$ and $HC_{cont}$ are expressed in milligrams of hydrocarbon compound per gram of rock, $S_{h0}$ is a measured amount of free hydrocarbon compounds released in step a), $S_{h1}$ is a measured amount of free hydrocarbon compounds released in step b), and $HC_{cont}$ is free hydrocarbon content.

26. The method as claimed in claim 24, wherein a production index is calculated according to the formula as follows:

$$PI_{shale} = \frac{(S_{h0} + S_{h1})}{(S_{h0} + S_{h1} + S_{h2})} \times 100$$

wherein $S_{h0}$, $S_{h1}$ and $S_{h2}$ are expressed in milligrams of hydrocarbon compound per gram of rock where $S_{h0}$ is a measured amount of free hydrocarbon compounds released in step a), $S_{h1}$ is a measured amount of free hydrocarbon compounds released in step b), $S_{h2}$ is a measured amount of free hydrocarbon compounds released in step c), and $PI_{shale}$ is the production index expressed as a percentage by mass.

27. The method as claimed in claim 14, wherein the first and second time durations range between 2 and 4 minutes.

28. A method for determining quantities of hydrocarbon compounds contained in hydrocarbon source rock obtained from a geological sample by pyrolysis of the hydrocarbon source rock from the geological sample by heating the hydrocarbon source rock from the geological sample in an inert atmosphere during a temperature sequence, comprising:

a) raising a temperature of the hydrocarbon source rock from the geological sample from a first temperature ranging between 50° C. and 120° C., according to a first temperature gradient ranging between 1° C./min and 50° C./min, to a second temperature ranging between 180° C. and 220° C., maintaining the hydrocarbon source rock from the geological sample at the second temperature for a first predetermined time duration of greater than one half minute and measuring a quantity of hydrocarbons released from the hydrocarbon source rock from the geological sample during the heating of the hydrocarbon source rock from the geological sample for the first predetermined time duration;

b) raising the temperature of the hydrocarbon source rock from the geological sample from the second temperature according to a second temperature gradient ranging between 1° C./min and 50° C./min to a third temperature ranging between 330° C. and 370° C., maintaining the hydrocarbon source rock from the geological sample at the third temperature for a second predetermined time duration of greater than one half minute and measuring a quantity of hydrocarbons released from the rock from the geological sample during the heating of the hydrocarbon source rock from the geological sample for the second predetermined duration;

c) raising the temperature of the hydrocarbon source rock from the geological sample from the third temperature according to a third temperature gradient ranging between 1° C./min and 50° C./min to a fourth temperature ranging between 630° C. and 670° C. and measuring a quantity of hydrocarbons released during the heating of the hydrocarbon source rock from the geological sample from the third temperature until the fourth temperature is reached.

29. The method as claimed in claim 28, wherein the first and second time durations range between 2 and 4 minutes.

30. A method for determining quantities of hydrocarbon compounds contained in hydrocarbon source rock, reservoir rock or source rock obtained from a geological sample by pyrolysis of the hydrocarbon source rock, reservoir rock or source rock from the geological sample by heating the hydrocarbon source rock, reservoir rock or source rock from the geological sample in an inert atmosphere during a temperature sequence, comprising:

a) raising a temperature of the hydrocarbon source rock, reservoir rock or source rock from the geological sample from a first temperature ranging between 50° C. and 120° C., according to a first temperature gradient ranging between 1° C./min and 50° C./min, to a second temperature ranging between 180° C. and 220° C., maintaining the hydrocarbon source rock, reservoir rock or source rock from the geological sample at the second temperature for a first predetermined time duration of greater than one half minute and measuring a quantity of hydrocarbons released from the hydrocarbon source rock, reservoir rock or source rock from the geological sample during the heating for the first predetermined time duration;

b) raising the temperature of the hydrocarbon source rock, reservoir rock or source rock from the geological sample from the second temperature according to a second temperature gradient ranging between 1° C./min and 50° C./min to a third temperature ranging between 330° C. and 370° C., maintaining the hydrocarbon source rock, reservoir rock or source rock from the geological sample at the third temperature for a second predetermined time duration of greater than one half minute and measuring a quantity of hydrocarbons released from the hydrocarbon source rock, reservoir rock or source rock from the geological sample during the heating for the second predetermined duration;

c) raising the temperature of the hydrocarbon source rock, reservoir rock or source rock from the geological sample from the third temperature according to a third temperature gradient ranging between 1° C./min and 50° C./min to a fourth temperature ranging between 630° C. and 670° C. and measuring a quantity of hydrocarbons released during the heating of the hydrocarbon source rock, reservoir rock or source rock from the geological sample from the third temperature until the fourth temperature is reached.

* * * * *

UNITED STATES PATENT AND TRADEMARK OFFICE
CERTIFICATE OF CORRECTION

PATENT NO. : 10,088,465 B2
APPLICATION NO. : 15/845710
DATED : October 2, 2018
INVENTOR(S) : Daniel Pillot et al.

Page 1 of 1

It is certified that error appears in the above-identified patent and that said Letters Patent is hereby corrected as shown below:

On the Title Page

Item (30) Under Foreign Application Priority Data:
Insert -- June 3, 2014 (FR) 14/55.009 --

Signed and Sealed this
Nineteenth Day of November, 2019

Andrei Iancu
*Director of the United States Patent and Trademark Office*